United States Patent
Sun et al.

(10) Patent No.: US 6,517,238 B2
(45) Date of Patent: Feb. 11, 2003

(54) THERMAL IMAGING MEASUREMENT OF LATERAL DIFFUSIVITY AND NON-INVASIVE MATERIAL DEFECT DETECTION

(75) Inventors: Jiangang Sun, Westmont, IL (US); Chris Deemer, Downers Grove, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/761,732

(22) Filed: Jan. 18, 2001

(65) Prior Publication Data

US 2002/0126730 A1 Sep. 12, 2002

(51) Int. Cl.[7] .............................................. G01N 25/20
(52) U.S. Cl. .............................. 374/43; 374/5; 374/126; 250/341.6; 702/136
(58) Field of Search ............................... 374/43, 44, 4, 374/5, 126; 250/341.6; 702/136

(56) References Cited

U.S. PATENT DOCUMENTS

| | | | | |
|---|---|---|---|---|
| 4,928,254 A | * | 5/1990 | Knudsen et al. | 374/43 |
| 5,044,767 A | * | 9/1991 | Gustafson | 374/43 |
| 5,582,485 A | * | 12/1996 | Lesniak | 374/5 |
| 5,667,300 A | * | 9/1997 | Mandelis et al. | 374/43 |
| 5,711,603 A | | 1/1998 | Ringermacher et al. | 374/5 |
| 6,343,874 B1 | * | 2/2002 | Legrandjacques et al. | 374/5 |
| 6,367,968 B1 | * | 4/2002 | Ringermacher et al. | 374/7 |
| 6,367,969 B1 | * | 4/2002 | Ringermacher et al. | 374/7 |

OTHER PUBLICATIONS

Sun et al., "Thermal Imaging Measurement and Correlation of Thermal Diffusivity in Continuous Fiber Ceramic Composites", Thermal Conductivity 24, Eds. Gaal and Apostolescu, pp. 616–622, (Jan. 11, 1999).*
Graham et al., "In–Plane Thermal Diffusivity Measurements of Orthotropic Materials," Thermal Conductivity 24, Eds. Gaal and Apostolescu, pp. 241–252, (Jan. 11, 1999).*
Ouyang et al., "Novel Measurement of Anisotropic Thermal Diffusivity"; Rev. Prog. Quant. NDE; vol. 17/A Eds. Thompson and Chimenti, Plenum Press, New York, pp. 453–456 (1998).*
Cramer et al., "The Application of Thermal Diffusivity Imaging to SIC–Fiber–Reinforced Silicon Nitride," Rev. Prog. Quant. NDE; vol. 12/B, Eds. Thompson and Chimenti, pp. 1305–1311, 1993.*
J.G. Sun, C. Deemer and W. A. Ellingson, *Thermal Imaging Measurement of Lateral Thermal Diffusivity in Continuous Fiber Ceramic Composites*, Jan. 23–28, 2000. Conference Paper.

* cited by examiner

*Primary Examiner*—Diego Gutierrez
*Assistant Examiner*—Stanley J. Pruchnic, Jr.
(74) *Attorney, Agent, or Firm*—Bradley W. Smith; Mark P. Dvorscak; Paul A. Gottlieb

(57) ABSTRACT

A system and method for determining lateral thermal diffusivity of a material sample using a heat pulse; a sample oriented within an orthogonal coordinate system; an infrared camera; and a computer that has a digital frame grabber, and data acquisition and processing software. The mathematical model used within the data processing software is capable of determining the lateral thermal diffusivity of a sample of finite boundaries. The system and method may also be used as a nondestructive method for detecting and locating cracks within the material sample.

12 Claims, 5 Drawing Sheets t = 0.17 s

THERMAL IMAGING MEASUREMENT OF LATERAL DIFFUSIVITY AND NON-INVASIVE MATERIAL DEFECT DETECTION

U.S. GOVERNMENT RIGHTS

The United States Government has rights in this invention pursuant to Contract No. W-31-109-ENG-38 between the U.S. Department of Energy and University of Chicago.

BACKGROUND OF THE INVENTION

Thermal diffusivity, is a material property and relates to the transient heat transfer speed through the particular material. This property is dependent on the heat transfer direction for anisotropic materials. Anisotropic materials are materials that have different properties along lines of different directions. For planar samples, the normal thermal diffusivity is a property of the speed at which heat is transferred through the thickness of the sample from the side where the heat is applied to the side where heat was not applied. Lateral thermal diffusivity is a property of the speed at which heat is transferred in a perpendicular direction within the material relative to the direction from which the heat has been applied.

An infrared thermal imaging system is used to determine values for normal and lateral thermal diffusivity of a material sample. Thermal imaging systems typically consist of an infrared camera, a personal computer (PC) equipped with a digital frame grabber and data acquisition and processing software, a flash lamp as a heat source, and electronics to monitor and control the system operation. Using this equipment, a flash thermal imaging test is performed. During the test, pulsed heat energy is applied to the sample's back surface that has been partially shielded to prevent a portion of the material sample from being heated directly when the pulsed heat energy is applied. The change in temperature distribution on the opposite, front, surface is monitored by the infrared camera with a series of thermal images being captured and recorded within the PC.

The temperature distribution represents the effects of both the normal heat transfer through the thickness of the sample and the lateral heat transfer through the interface between the shielded and unshielded back-surface regions. The temperature distributions that are detected and recorded by the infrared camera are fitted with a theoretical solution of the heat transfer process to determine the lateral thermal diffusivity at the interface.

Zhong Ouyang, et. al. have published a method for measuring the lateral thermal diffusivity. Their theory was based on samples being infinite-sized plates, and required the manual fitting of the experimental data with the theoretical solution in spatial domain for single curves. Their theory also required the interface location to be pre-measured by hand and required even (uniform) heating. A solution for semi-infinite width $(0<x<\infty)$ sample was used by Ouyang et al. (1998), as:

$$T(x, L, t) = \frac{1}{2L}\left(\text{erfc}\frac{a-x}{2\sqrt{\alpha_x t}} + \text{erfc}\frac{a+x}{2\sqrt{\alpha_x t}}\right)\left[1 + 2\sum_{n=1}^{\infty}(-1)^n \exp\left(-\frac{n^2\pi^2}{L^2}\alpha_z t\right)\right],$$

where T is temperature; x is a point along an x-axis; L is sample thickness; t is time; a is the interface location along the x-axis; $\alpha_x$, and $\alpha_z$ are the lateral (along the x-axis) and through-thickness (along the z-axis) thermal diffusivities, respectively; and n corresponds to the number of terms used in the summation.

The present system and method for determining normal and lateral thermal diffusivity uses finite boundaries to determine the diffusivity. Ouyang's method simplifies the determination by using semi-infinite boundaries. The present system takes non-uniform heating into consideration by explicitly calculating the temperature amplitude at each pixel. The present system may also be used as a nondestructive method to detect and locate material defects within the sample (cracks perpendicular to the sample surface). The depth of a crack within the material can be determined by the defect's correlating diffusivity value. Existing nondestructive techniques for detecting material defects include ultrasound technology. However, ultrasound techniques are time consuming for detecting this type of defect in large material samples.

Transient thermography has been used for the nondestructive detection of material flaws (see U.S. Pat. No. 5,711,603, Ringermacher et al. ("'603"). The '603 patent describes a method for flaw depth detection using thermal imaging captured by an infrared camera. The thermal imaging technique used in the '603 patent applies pulsed thermal energy to the sample surface and subsequently a thin layer of material on the surface will be instantaneously heated to a high temperature. Heat transfer takes place from the surface that was heated to the interior of the sample resulting in a continuous decrease of the surface temperature. If a plain crack (a crack with a plane parallel to the sample surface that was heated) exists, the heat is restricted from further transfer deeper into the sample material. Therefore, the surface temperature at this region will remain higher than in surrounding areas so that the sample material above the plain crack will be viewed as a "hot spot" by the infrared receptors. The hot spot will occur earlier during the analysis if the crack is shallow and will appear later in the analysis if the crack is deeper. In '603 a correlation was developed between the measured time when the highest hot spot contrast occurs and relative depth of the crack within the sample. The analysis was performed pixel by pixel and the final relative depth for all pixels is composed into an image (or map). The relative depth is color coded and presented as the result.

Differences between the '603 patent and the present system include the type of crack or defect that may be detected. The '603 patent detects plain cracks that are completely within the material and are oriented parallel to the heated sample surface (like an air gap or delamination defect). The present invention detects cracks that are perpendicular to the heated surface and these cracks may be of varying depths that include surface cracks. The '603 patent uses an empirical correlation between time of hot spot occurrence and crack depth. The present system fits experimental temporal-spatial curves with a theoretical model. The '603 patent also derives an image of relative depth of defect from the surface while the present system derives the depth (or length) of the crack extending from the surface to the inside of the sample.

OBJECTS OF THE INVENTION

The object of this invention is to provide an automated and accurate method for determining the lateral thermal diffusivity of a material sample using a model that contains finite boundaries.

Another object of this invention is to provide a nondestructive method for the detection of cracks within a material sample by use of the method used to determine thermal diffusivity.

SUMMARY OF THE INVENTION

A system and method for determining lateral thermal diffusivity of a material sample using a heat pulse; a sample oriented within an orthogonal coordinate system; an infrared camera; and a computer that has a digital frame grabber, and data acquisition and processing software. The mathematical model used within the data processing software is capable of determining the thermal diffusivity of a sample of finite boundaries. The system and method may also be used as a nondestructive method for detecting and locating cracks within the material sample.

DETAILED DESCRIPTION OF THE PREFERRED EMBODIMENT

Figure 1:
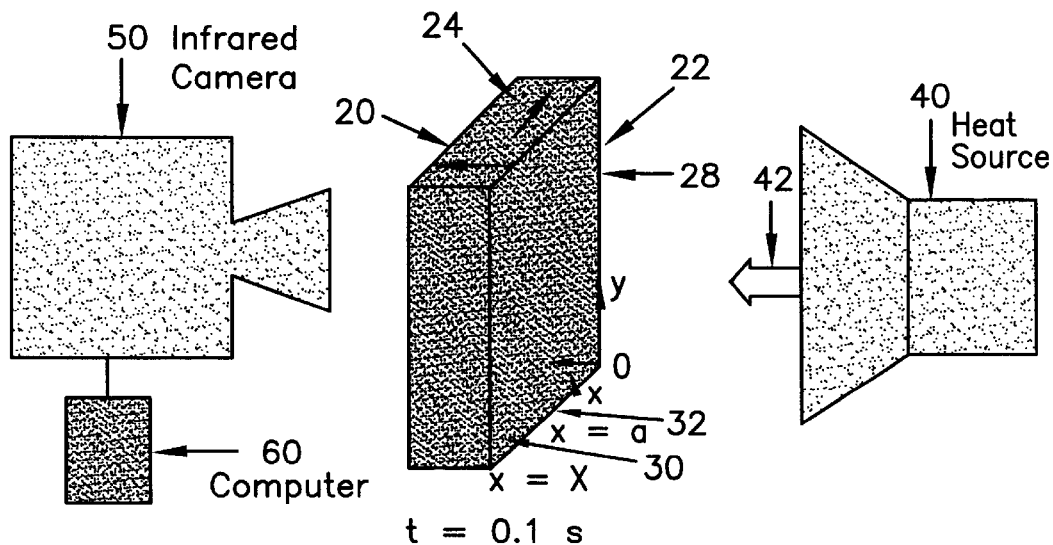
FIG. 1 is the system set up for determining diffusivities.

FIG. 1 depicts the system set up 10. A material sample 20 is placed between a heat source 40, that has an average direction of heat flow 42 when the heat source 40 is activated, and an infrared camera 50 that has infrared receptors directed toward the sample 20. The sample 20 is oriented within an orthogonal coordinate system having x, y, and z-axes. The x-y plane of the coordinate system is perpendicular to the average direction of heat flow 42 while the z-axis is essentially parallel to the average direction of heat flow 42. A shield 22 on the back side (the side facing the heat source 40) of the sample 20 insulates the portion of the sample 20 that is covered by the shield 22 from receiving heat from the heat source 40 when the heat source 40 is activated. An edge of the shield 22 creates an interface 32 between the shielded portion of the sample 28 and the unshielded portion of the sample 30. The interface 32 is essentially equidistant from the y-axis. The infrared camera 50 is coupled to a personal computer (PC) 60. The PC 60 is equipped with a digital frame grabber and data acquisition and data processing software.

To determine lateral thermal diffusivity using this set up 10, the heat source 40 is activated and a heat pulse heats the unshielded portion of the sample 30. The unshielded portion of the sample 30 absorbs the heat pulse and heat energy is diffused through the sample at a rate determined by the specific properties of the material that makes up the sample 20. Heat energy diffuses in the z-direction (through the sample's 20 thickness) and laterally (in the x-direction). Methods for through-thickness (normal) diffusivity, $\alpha_z$, were developed in the 1960s. Therefore, the normal thermal diffusivity is not directly measured using this set up 10 because such values are readily available and are considered known values for the samples. There will be no heat flow through the sample 20 in the y-direction using this system 10 with a flat rectangular sample 20 unless the sample 20 contains internal defects.

Previous techniques can not process thermal data with a non-uniform heating effect. For any technique, the experimental set-up should be designed to provide as uniform heating as possible. However, non-uniform heating may be the result of varying optical properties on the surface of a single sample. For example, a black surface usually exhibits high surface absorptivity, the ceramic composite sample used for data in FIGS. 2–5 should have an absorptivity larger than 0.9 (maximum absorptivity is 1.0). If a sample has surface contamination and one part of the sample has an absorptivity of 0.8 and another part of 0.9, then after heating, the first part may reach a surface temperature of 80° C., but the second part will have a surface temperature of 90° C. (this may be considered non-uniform heating). The present invention handles these temperature differences by explicitly calculating the temperature amplitude at each pixel.

As the heat energy diffuses through the sample 20 with time, the infrared camera 50 receives thermal images in a 256×256 focal plane array of infrared detectors. Therefore there are 256 pixels along the x-axis and 256 pixels along the y-axis of the sample 20. The digital frame grabber software on the PC 60 stores the images. The data acquisition and data processing software will record individual temperature values of the sample 20 as perceived at each pixel within the infrared camera 50. The recorded temperature and corresponding location on the sample 20 will be compared to a theoretical temperature distribution according to the equation:

$$T(x, L, t) = \frac{a}{XL}\left[1 + 2\sum_{m=1}^{\infty}\frac{X}{m\pi a}\sin\frac{m\pi a}{X}\cos\frac{m\pi x}{X}\exp\left(-\frac{m^2\pi^2}{X^2}\alpha_x t\right)\right] \quad \text{(Eq. 1)}$$

$$\left[1 + 2\sum_{n=1}^{\infty}(-1)^n\exp\left(-\frac{n^2\pi^2}{L^2}\alpha_z t\right)\right],$$

where T is theoretical temperature; x is a corresponding point along the x-axis; L is the thickness of the sample 20 along the z-axis; X is the overall width of the sample 20; t is time; a is the interface location 32 along the x-axis; $\alpha_x$ and $\alpha_z$ are a lateral (along said x-axis) and a normal (along said z-axis) thermal diffusivity, respectively; and m and n correspond to the number of terms used in their respective summations.

Equation 1 is derived for the heat transfer process as examined under ideal conditions, this equation should match perfectly with the experimental data (for every pixel and at every time instant) provided that all parameters used in this equation are correct. Parameters already known include: sample thickness L, sample width X, through-thickness diffusivity $\alpha_z$, as these values are previously measured; we also know pixel position $x_i$ and time t when each image is taken. The only unknown parameters in the above equation are $\alpha_x$ and $\alpha$. The main objective of this invention is to find the correct values of $\alpha_x$ and a so the theoretical curve (calculated from the above equation) will have a best match of experimental data (curves).

Figure 2:
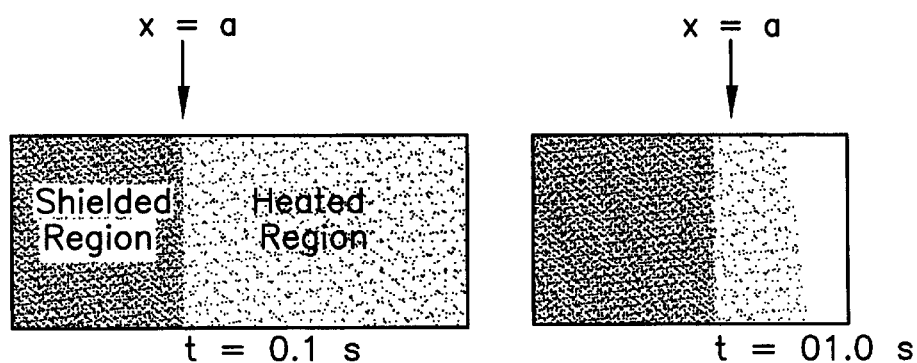
FIG. 2 depicts infrared images taken at t=0.1 s and t=1.0 s after the heat pulse for a ceramic composite.

FIG. 2 depicts two typical thermal images taken at times t=0.1 s and t=1.0 s (the complete set of data contains 101 images taken at t=0, 0.01, 0.02, . . . 1.0 s). The images in FIG. 2 each have 185 pixels in the x-direction (width) and 80 pixels in the y-direction (height). Therefore, the corresponding data has 80×185-pixel lines with temperature distributions measured at intervals of 0.01 s from t=0 s to t=1 s for each line. If the sample 20 is uniform, the lateral heat transfer occurs only in the x-direction and lateral thermal diffusivity is a constant at any y location. This situation is the ideal 2-dimensional heat transfer condition as assumed in Eq. 1 above. Under these conditions, the heat transfer data at one y= constant line may be analyzed to determine $\alpha_x$ as the lateral thermal diffusivity at x=$\alpha$. When the sample 20 is not uniform (due to material variation or defect), every y= constant line (all 80 lines for the sample shown in FIG. 2) must be analyzed to obtain an $\alpha_x$ distribution along the interface line (along the y-direction), i.e., $\alpha_x$ distribution in 0<y<Y at x=$\alpha$.

Data processing for each line begins with inputting initially estimated values for lateral thermal diffusivity, $\alpha_x$, and interface location, a. The analysis is performed one line at a time.

Figure 3:
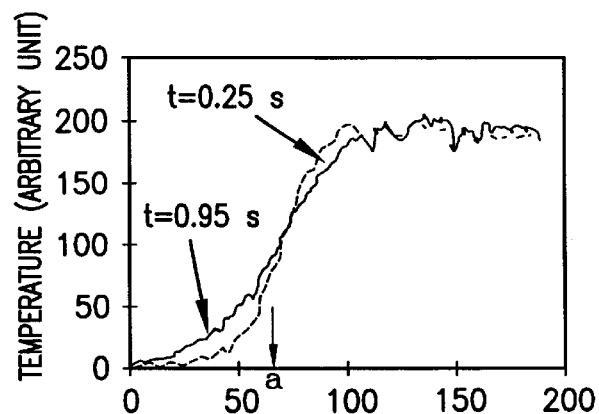
FIG. 3 depicts the measured temperature distributions at t=0.25 and 0.95 s after flash along a typical horizontal line shown in FIG. 2.

The goal is to fit the theoretical temperature distribution curves from Eq. 1 with measured temperature distributions at all time steps. The best fit between the theoretical and measured distributions gives the correct lateral thermal diffusivity, $\alpha_x$, and interface location, a. FIG. 3 illustrates the measured temperature distributions at t=0.25 s and t=0.95 s for the images shown in FIG. 2 after the heat pulse was released from the heat source 40.

To fit the theoretical distribution with the measured temperature distribution for each pixel, the values for lateral diffusivity, $\alpha_x$, and interface location, a, are initially estimated and the theoretical temperature value from Eq. 1 above is compared with the measured and recorded value for each x location by use of a least-square fit equation:

$$F = \sum_t \sum_i w_i [A_i T(x_i, L, t) - T_i(t)]^2. \quad \text{(Eq. 2)}$$

The initially guessed values for a and $\alpha$ are inserted into Equation 1 to obtain a temperature at every pixel and every time instant. The total error between the calculated temperature and measured temperature is F as determined by Equation 2. When there is a perfect match (ideal condition and with correct values of $\alpha_x$ and $\alpha$), F=0; but due to experimental noise and/or other factors, F is always experimentally larger than zero. The minimum F (i.e., at the smallest match error) should give the correct values of $\alpha_x$ and $\alpha$. The Newton method is then used to derive a new guess of $\alpha_x$ and a values so F is minimized, this is one cycle of the iteration. Many iterations are needed to finally obtain the correct $\alpha_x$ and a values such that F is minimized.

For the example shown in FIGS. 2 and 3, at pixel i (0≦i≦184), denote $A_i$ as temperature amplitude to be determined and $x_i$ as x-coordinate at pixel i, then the theoretical temperature prediction $A_i T(x_i, L, t)$ (where $T(x_i, L, t)$ is from Eq. 1) and measured temperature $T_i(t)$ (obtained from thermal imaging data) as functions of time (at times t=0, 0.01, 0.02, , 1.0 s). Because both $T(x_i, L, t)$ and $T_i(t)$ are known, a simple least-square fit of these two time-history curves determines the amplitude $A_i$ at pixel i. This process is repeated to obtain $A_i$ for all pixels in the current horizontal line.

The thermal imaging data in FIG. 3 show that the change of temperature due to lateral heat transfer occurs only near the interface location at x=a. Therefore, when performing data fitting, the data near the interface 32 should receive bigger weight than those far away from the interface 32. By doing so, the fitting accuracy will be improved. To establish the weighting function, the slope of each temperature distribution curve (along x-direction at fixed time) is calculated. The slope curves at all time steps are then averaged and normalized (i.e., maximum at 1), and the area under the average-normalized slope curve is calculated (denoted as W). The weighting function is then defined as a normal distribution function centered at a:

$$w_i = \exp\left[-\pi\left(\frac{x_i - a}{W}\right)^2\right] \quad 0 \le i \le 184, \quad \text{(Eq. 3)}$$

where a is the interface location 32.

Figure 4:
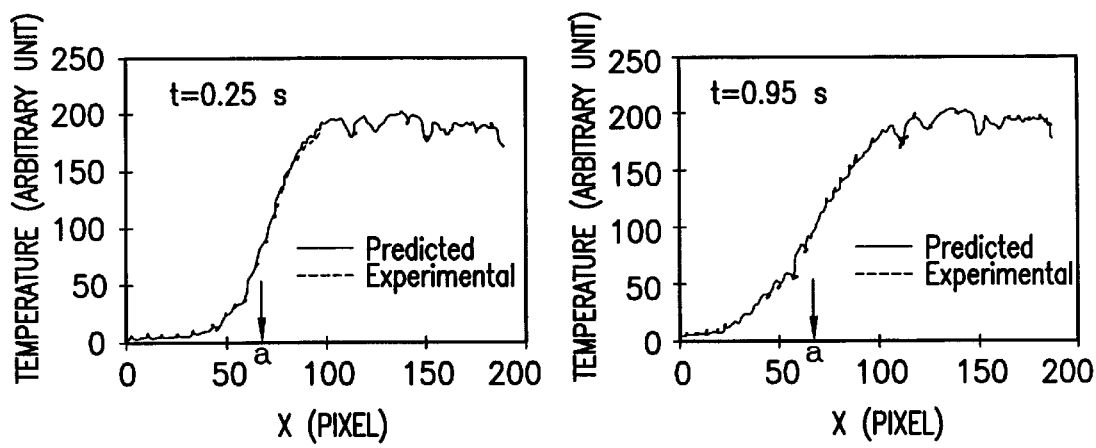
FIG. 4 is a comparison of predicted and experimental temperature distributions at t=0.25 s and 0.95 s.

After fitting function F is calculated from Eq. 2, new $\alpha_x$ and $\alpha$ values are predicted by Newton iteration scheme to minimize F. These new values are used as new guesses in next iteration. Iterations of this type continue until F is minimized (or approaches the best fit). The predicted $\alpha_x$ and $\alpha$ values converge to the correct values when using simulated analytical data. A comparison of predicted and experimental temperature distributions is shown in FIG. 4.

Figure 5:
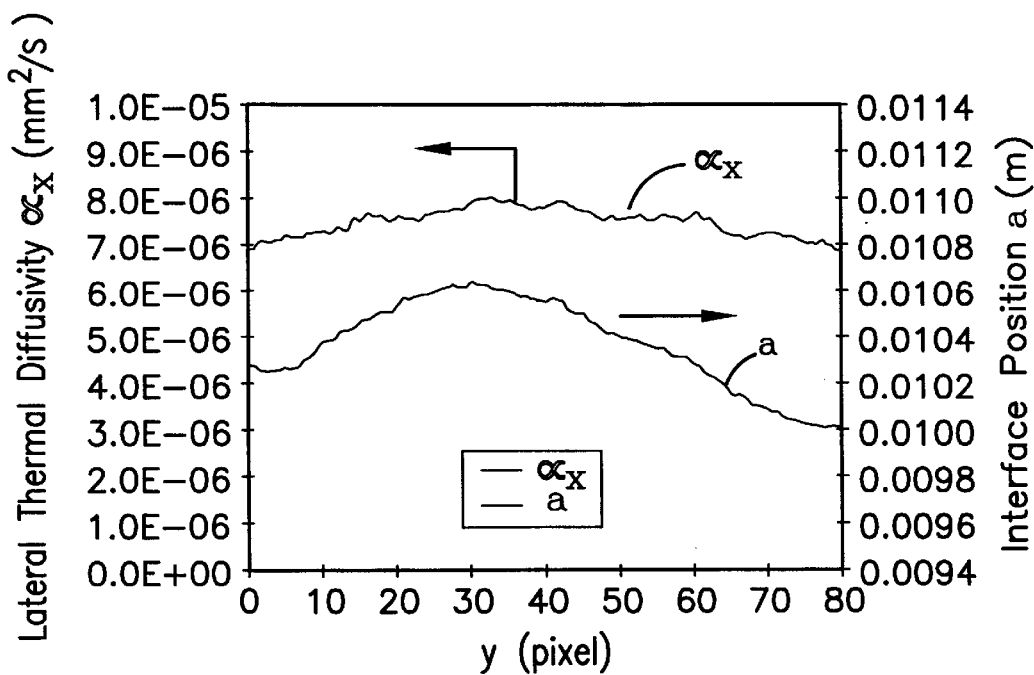
FIG. 5 depicts predicted $\alpha_x$, and $\alpha$ distributions along the y-direction for the ceramic composite sample of FIGS. 2 and 3.

The steps of initially guessing values for $\alpha_x$ and $\alpha$; determining the temperature amplitude at each pixel; applying a weighting function; applying a fitting function; and iterations to determine $\alpha_x$ and $\alpha$, can be repeated for all lines in the y-direction (80 lines for the example shown in FIGS. 2 and 3). FIG. 5 shows the predicted $\alpha_x$ and $\alpha$ distributions along the y-direction for the ceramic composite sample used in FIGS. 2 and 3.

Nondestructive evaluation (NDE) or detection of cracks within the sample 20 can be accomplished using this system 10. Through-thickness cracks are typically not detected by through-thickness NDE techniques such as through-thickness (normal) thermal diffusivity, transmission ultrasound, and x-ray imaging. However, such cracks or defects can easily be detected and characterized by lateral thermal diffusivity measurement.

Figure 6:
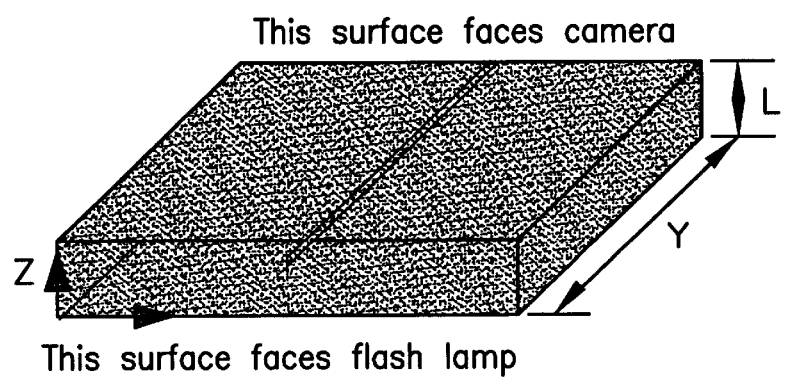
FIG. 6 shows an aluminum alloy sample with a cut of three different depths.
Figure 7:
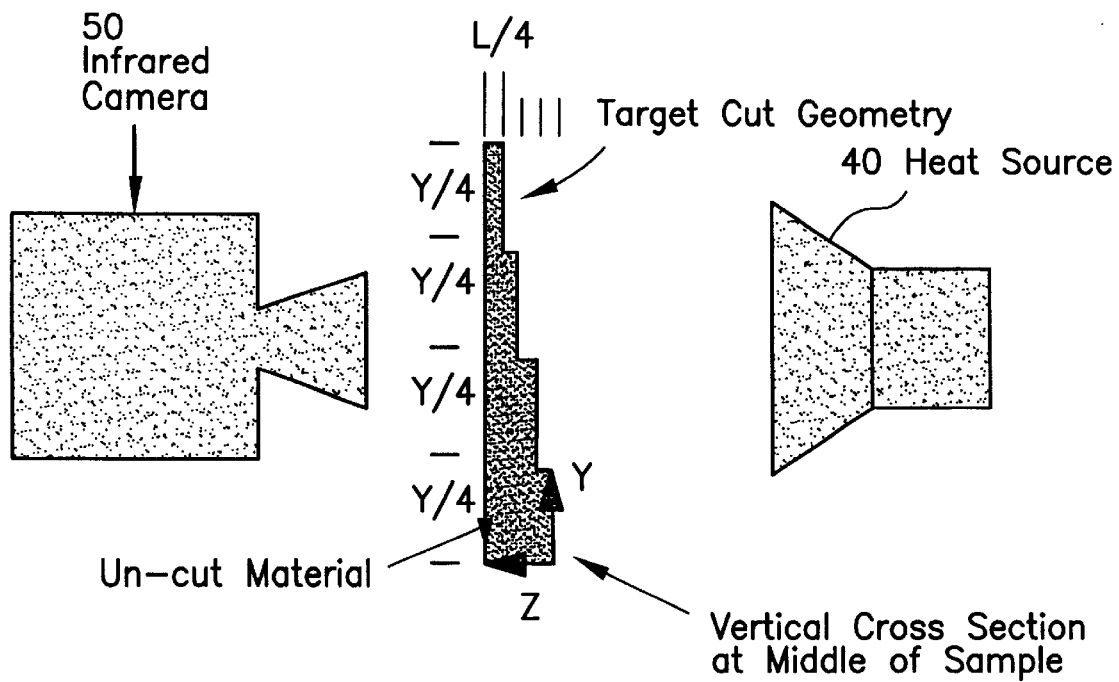
FIG. 7 is the system set up for NDE testing of the aluminum alloy sample.
Figure 8:
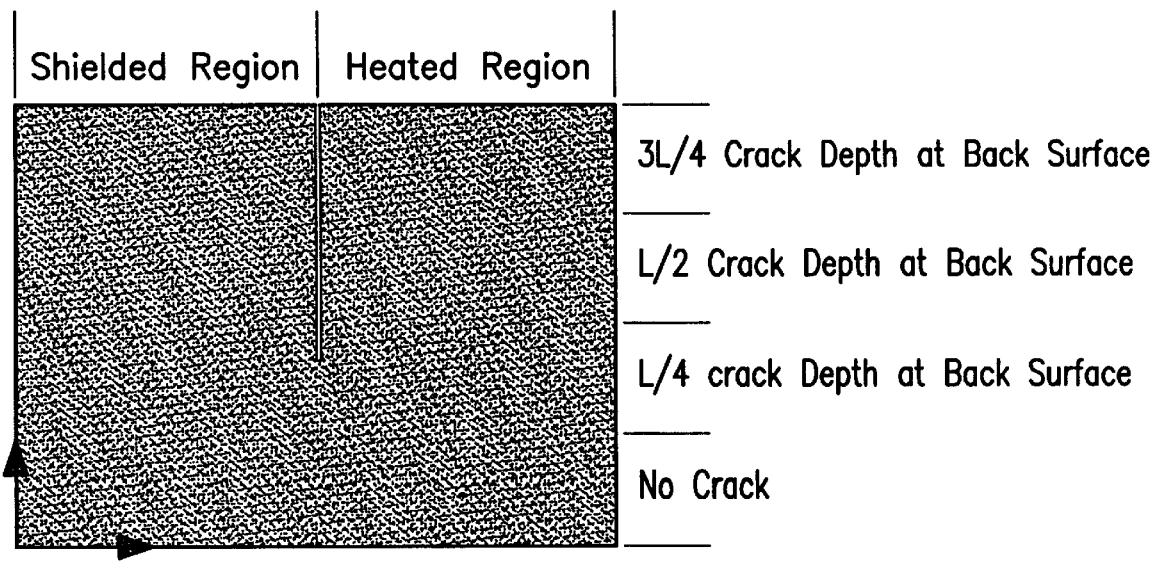
FIG. 8 is a schematic of the surface viewed by the infrared camera indicating expected heat flows.

FIG. 6 shows an aluminum alloy sample with a vertical cut of three depths at the middle width (x-direction). The target cut depths are ¾, ½, and ¼ of the thickness and each cut length is ¼ of the sample height (y-direction). There is not a cut at the bottom ¼ of the height. The set up for NDE is shown in FIG. 7. The cut surface faces the heat source 40 and the smooth surface faces the infrared camera 50. The interface is vertical along the cut. It is expected that the heat will diffuse in the lateral y-direction in addition to diffusing in the x-direction because the dominant lateral heat flow in the x-direction is not uniform. An illustration of this heat flow scheme is shown in FIG. 8. The y-direction heat flow will reduce the sensitivity and resolution in detecting the tip of the defect where the depth of the cut changes.

Figure 9:
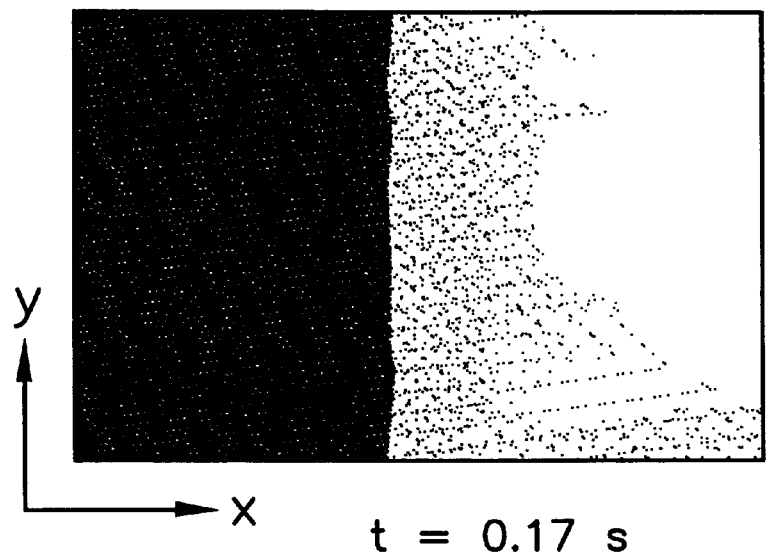
FIG. 9 is a thermal image taken at t=0.17 s after the heat pulse for the aluminum alloy sample of FIGS. 6 and 7.
Figure 10:
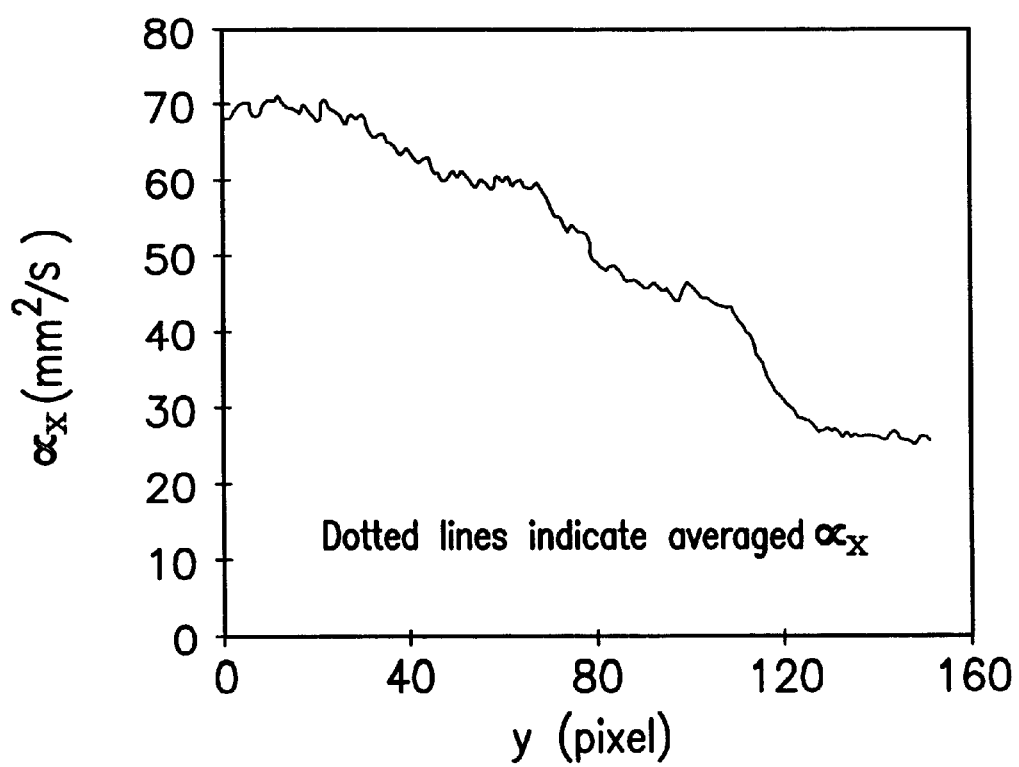
FIG. 10 depicts predicted $\alpha_x$ along the y-direction for the aluminum alloy sample of FIGS. 6 and 7.

FIG. 9 shows a thermal image taken at 0.17 s after the heat pulse has been delivered. It is evident that the heat flow is stronger at the bottom of the image than at the top because the cut is deeper at the top. The predicted lateral thermal diffusivity $\alpha_x$ along the sample height (y-direction) is plotted in FIG. 10. The average values of $\alpha_x$ at all four regions of thickness are plotted at dotted lines and are listed in Table 1.

TABLE 1

List of predicted values of lateral thermal diffusivity $\alpha_x$

| Cut depth (%) | Predicted $\alpha_x$ (mm²/s) | $\alpha_x$ reduction (%) |
|---|---|---|
| 0 | 70 | 0 |
| 25 | 60 | 14 |
| 50 | 45 | 36 |
| 75 | 25 | 64 |

The predicted lateral thermal diffusivity is sensitive to cut depth. It should be noted that cut depths listed in Table 1 are target values for machining and could not be directly measured due to the thinness of the sample and the cut width. The sample can be scanned for cracks by placing the vertical shielding material at various x-locations and the resulting $\alpha_x$ distributions (each as that in FIG. 10) can be plotted into a 2-dimensional image to reveal the location and intensity of the through-thickness defect.

What is claimed is:

1. A system for determining thermal diffusivity in a material sample, comprising:

a heat source having an average direction of heat flow directed toward a plurality of infrared receptors associate with an infrared camera; where said infrared receptors are directed in approximate opposition to said average direction of heat flow from said heat source;

a sample located between said heat source and said infrared camera such that said sample intercepts a heat flow from said heat source, said sample having a back side and a front side with said back side facing said heat source and said front side facing said infrared camera, said sample defining an orientation of an orthogonal coordinate system having axes x, y and z, such that an x-y plane of said coordinate system is perpendicular to said average direction of said heat flow from said heat source when said heat source is energized and where said z axis is essentially parallel to said average direction of heat flow;

a heat insulating shield positioned to cover a portion of said back side of said sample where said heat shield is sized to cover all of said sample located behind said heat shield providing a shielded sample portion and where an interface edge of said shield defines an interface between said shielded sample portion of said sample and an unshielded sample portion which comprises the remainder of said sample in said x-y plane where said interface edge extends across said sample along a linear axial projection effectively bisecting said sample along an axial line; and a computer coupled to said infrared camera, said computer having a plurality of software capable of data acquisition and data processing where said computer receives and records temperature changes with time as sensed by said infrared receptors after a pulse of heat has been emitted from said heat source and compares said recorded temperatures within an equation:

$$T(x, L, t) = \frac{a}{XL}\left[1 + 2\sum_{m=1}^{\infty} \frac{X}{m\pi a}\sin\frac{m\pi a}{X}\cos\frac{m\pi x}{X}\exp\left(-\frac{m^2\pi^2}{X^2}\alpha_x t\right)\right]$$

-continued $$\left[1 + 2\sum_{n=1}^{\infty}(-1)^n\exp\left(-\frac{n^2\pi^2}{L^2}\alpha_z t\right)\right]$$

when said interface is oriented along a designated y axis partly covering said sample and where T is temperature; x is a point along said x axis; L is a sample thickness measured along said z axis; t is time; X is a width of said sample as measured along said x axis; $\alpha_x$ and $\alpha_z$ are a lateral (along said x-axis) and a normal (along said z-axis) thermal diffusivity, respectively; and m and n correspond to a number of terms used in a respective summation where said equation is numerically solved for said lateral and said normal diffusivities.

2. A method for determining lateral thermal diffusivity in a material sample, comprising the steps of:

positioning a heat source so that when said heat source is energized it produces a heat flow having an average direction of heat flow;

positioning an infrared camera having a plurality of infrared receptors such that said infrared receptors are directed in opposition to said average direction of heat flow;

positioning a sample between said heat source and said camera and at a specified distance from said heat source and within an orthogonal coordinate system having an origin and axes x, y and z, such that an x-y plane of said coordinate system is perpendicular to said average direction of said heat flow from said heat source when said heat source is energized and where said z axis is essentially parallel to said average direction of heat flow;

selecting a heat shield having a straight linear edge or interface, a continuous unpenetrated surface and sized so that said heat shield equals or exceeds said sample in surface area within said x-y plane allowing said heat shield to completely cover a portion of said sample not selectively exposed by positioning said interface of said heat shield with the result that said heat shield effectively divides said sample into a shielded portion and an unshielded portion along said interface;

placing said heat shield on a back side of said sample facing said heat source and and orienting said heat shield so that said straight edge or interface is parallel with said y axis;

placing said interface at a distance "a" from said y axis as measured along said x axis so that a plurality of points along said interface are equidistant from said y axis;

applying a pulse of heat energy from said heat energy source to said sample such that an unshielded area absorbs part of said energy while said shielding material prevents a shielded area from absorbing part of said energy;

receiving a digitized thermal image of said sample with time as said energy diffuses through said sample where said image is generated by thermal information sensed by infrared receptors incorporated in said camera on a front side of said sample;

recording a digitized thermal image of of said sample with time as said energy diffuses through said sample from said back side to said front side;

numerically generating a theoretical temperature distribution, T, response over time, t, through a thickness, L, of said sample according to an equation:

$$T(x, L, t) = \frac{a}{XL}\left[1 + 2\sum_{m=1}^{\infty} \frac{X}{m\pi a}\sin\frac{m\pi a}{X}\cos\frac{m\pi x}{X}\exp\left(-\frac{m^2\pi^2}{X^2}\alpha_x t\right)\right]$$

$$\left[1 + 2\sum_{n=1}^{\infty}(-1)^n \exp\left(-\frac{n^2\pi^2}{L^2}\alpha_z t\right)\right];$$

where x is a point along said x-axis; X is a sample width; $\alpha_x$ and $\alpha_z$ are a lateral (along said x-axis) and a normal (along said z-axis) thermal diffusivity, respectively; and m and n correspond to a number of terms used in a respective summation;

fitting said theoretical temperature distribution with a measured temperature distribution at each of several time steps and for each of several pixels by:
inputting initially guessed values for $a_x$ and a into said equation; and
comparing said theoretical temperature value from said equation for each value of x with said recorded temperature value at each x location by use of a least-square fit of said temperature values; and
numerically solving said equation for said interface, and said lateral diffusivity.

3. The method according to claim 2, further comprising the step of:
obtaining a modulation distribution by applying said equation to fit a temporal datum at each of several pixels within said infrared camera to derive a temperature amplitude, $A_i$, at each of said pixels.

4. The method according to claim 3, further comprising the step of:
assigning larger weight to a datum that is closer to said interface located at a, as compared to a datum that is farther away from said interface by applying a weighting function as a normal distribution function centered at said interface, a to each of said datum points generated by said thermal imaging:

$$w_i = \exp\left[-\pi\left(\frac{x_i - a}{W}\right)^2\right]$$

where W is an area under an average, normalized slope curve of measured temperature distributions and $w_I$ is a weighting function used to bias a set of obtained data so that data obtained in a neighborhood of a point close to said interface is given a greater weight than one further away from said interface;
employing said weighting function in an iterative technique to determine a correct value for said lateral diffusivity, $\alpha_x$, through the use of an equation for calculating a total error between a calculated temperature and a measured temperature, F, where $$F = \sum_t \sum_i w_i [A_i T(x_i, L, t) - T_i(t)]^2$$

$A_i$=Temperature Amplitude;
$T(x_i, L, t)$=Temperature as calculated in claim 2;
$T_i(t)$=Measured temperature from thermal imaging;
t=Time; and
i=Location designator.

5. The method according to claim 2, wherein said material sample is selected from a group consisting of: metal alloys and continuous fiber ceramic composites.

6. The method according to claim 2, wherein said shielding material is a material that insulates said sample from said heat source.

7. The method according to claim 2, wherein said heat energy source is a flash lamp.

8. The method according to claim 2, wherein said infrared camera has a focal plane array of 256×256 InSb (Indium Antimonide) sensors.

9. A method for determining lateral thermal diffusivity in a material sample, comprising the steps of:
positioning a heat source so that when said heat source is energized it produces a heat flow having an average direction of heat flow;
positioning an infrared camera such that an infrared receptor for said camera is directed in opposition to said average direction of heat flow;
positioning a sample between said heat source and said camera and at a specified distance from said heat source and within an orthogonal coordinate system having axes x, y and z, such that an x-y plane of said coordinate system is perpendicular to said average direction of said heat flow from said heat source when said heat source is energized and where said z axis is essentially parallel to said average direction of heat flow;
placing a shielding material on a back side of said sample facing said heat source and from an edge of said sample such that interface, a, is defined where a is measured along said x axis such that said interface, a, is equidistant along said y axis as measured from said x axis;
applying a pulse of heat energy from said heat energy source to said sample such that an unshielded area absorbs part of said energy while said shielding material prevents a shielded area from absorbing part of said energy;
receiving a digitized thermal image of said sample with time as said energy diffuses through said sample where said image is generated by thermal information sensed by infrared receptors incorporated in said camera on a front side of said sample;
recording a digitized thermal image of of said sample with time as said energy diffuses through said sample from said back side to said front side;
numerically generating a theoretical temperature distribution, T, response over time, t, through a thickness, L, of said sample according to an equation:

$$T(x, L, t) = \frac{a}{XL}\left[1 + 2\sum_{m=1}^{\infty} \frac{X}{m\pi a}\sin\frac{m\pi a}{X}\cos\frac{m\pi x}{X}\exp\left(-\frac{m^2\pi^2}{X^2}\alpha_x t\right)\right]$$

$$\left[1 + 2\sum_{n=1}^{\infty}(-1)^n \exp\left(-\frac{n^2\pi^2}{L^2}\alpha_z t\right)\right];$$

where x is a point along said x-axis; X is a sample width; $\alpha_x$ and $\alpha_z$ are a lateral (along said x-axis) and a normal (along said z-axis) thermal diffusivity, respectively; and m and n correspond to a number of terms used in a respective summation;

fitting said theoretical temperature distribution with a measured temperature distribution at each of several time steps and for each of several pixels by:
inputting initially guessed values for $a_x$ and a into said equation; and
comparing said theoretical temperature value from said equation for each value of x with said recorded temperature value at each x location by use of a least-square fit of said temperature values;

assigning larger weight to a datum that is closer to said interface located at a, as compared to a datum that is farther away from said interface by applying a weighting function as a normal distribution function centered at said interface, a to each of said datum points generated by said thermal imaging:

$$w_i = \exp\left[-\pi\left(\frac{x_i - a}{W}\right)^2\right]$$

where W is an area under an average, normalized slope curve of measured temperature distributions;

fitting said temperature, T, distributions at all time steps, t, to determine an interface location, a;

fitting said temperature, T, distributions at all time steps, t, to determine a value for lateral thermal diffusivity, $\alpha_x$; and determining a lateral diffusivity distribution along said interface at x=a by calculating the $\alpha_x$ and a at each of several lines defined by y is constant.

10. A method for determining lateral thermal diffusivity in a material sample, comprising the steps of:

positioning a heat source so that when said heat source is energized it produces a heat flow having an average direction of heat flow;

positioning an infrared camera such that an infrared receptor for said camera is directed in opposition to said average direction of heat flow;

positioning a sample between said heat source and said camera and at a specified distance from said heat source and within an orthogonal coordinate system having axes x, y and z, such that an x-y plane of said coordinate system is perpendicular to said average direction of said heat flow from said heat source when said heat source is energized and where said z axis is essentially parallel to said average direction of heat flow;

placing a shielding material on a back side of said sample facing said heat source and from an edge of said sample such that interface, a, is defined where a is measured along said x axis such that said interface, a, is equidistant along said y axis as measured from said x axis;

applying a pulse of heat energy from said heat energy source to said sample such that an unshielded area absorbs part of said energy while said shielding material prevents a shielded area from absorbing part of said energy;

receiving a digitized thermal image of said sample with time as said energy diffuses through said sample where said image is generated by thermal information sensed by infrared receptors incorporated in said camera on a front side of said sample;

recording a digitized thermal image of of said sample with time as said energy diffuses through said sample from said back side to said front side;

numerically generating a theoretical temperature distribution, T, response over time, t, through a thickness, L, of said sample according to an equation:

$$T(x, L, t) = \frac{a}{XL}\left[1 + 2\sum_{m=1}^{\infty}\frac{X}{m\pi a}\sin\frac{m\pi a}{X}\cos\frac{m\pi x}{X}\exp\left(-\frac{m^2\pi^2}{X^2}\alpha_x t\right)\right]$$

$$\left[1 + 2\sum_{n=1}^{\infty}(-1)^n\exp\left(-\frac{n^2\pi^2}{L^2}\alpha_z t\right)\right];$$

where x is a point along said x-axis; X is a sample width; $\alpha_x$ and $\alpha_z$ are a lateral (along said x-axis) and a normal (along said z-axis) thermal diffusivity, respectively; and m and n correspond to a number of terms used in a respective summation;

fitting said theoretical temperature distribution with a measured temperature distribution at each of several time steps and for each of several pixels by:

inputting initially guessed values for $a_x$ and a into said equation; and comparing said theoretical temperature value from said equation for each value of x with said recorded temperature value at each x location by use of a least-square fit of said temperature values;

fitting said temperature, T, distributions at all time steps, t, to determine an interface location a;

fitting said temperature, T, distributions at all time steps, t, to determine a value for lateral thermal diffusivity, $\alpha_x$; and determining a lateral diffusivity distribution along said interface at x=a by calculating the $\alpha_x$ and a at each of several lines defined by y is constant.

11. The method according to claim 10, further comprising the step of:

detecting defects within said sample by observing an infrared thermal image captured by said infrared camera and noting differences in thermal diffusivity along a y-axis.

12. The method according to claim 11, further comprising the step of:

scanning said sample for defects by placing said shielding at various locations along an x-axis.

* * * * *